United States Patent [19]
DeBoer et al.

[11] 4,113,855
[45] Sep. 12, 1978

[54] COMPOSITION OF MATTER AND PROCESS

[75] Inventors: Clarence DeBoer, Kalamazoo; Lester A. Dolak, Plainwell; Durey H. Peterson, Kalamazoo, all of Mich.

[73] Assignee: The Upjohn Company, Kalamazoo, Mich.

[21] Appl. No.: 834,285

[22] Filed: Sep. 19, 1977

[51] Int. Cl.² ............................................. A61K 35/00
[52] U.S. Cl. ..................................................... 424/117
[58] Field of Search .......................................... 424/117

[56] References Cited
U.S. PATENT DOCUMENTS 3,849,398  11/1974  Arai et al. ............................. 424/180

OTHER PUBLICATIONS

Watanabe et al., Jacs 94: pp. 3272–3274, (1972).

Primary Examiner—Jerome D. Goldberg
Attorney, Agent, or Firm—Roman Saliwanchik

[57] ABSTRACT

Novel antibiotic formulations of antibiotic 354 (U-54,703) and their use in treating susceptible infectious disease in humans and animals.

8 Claims, 3 Drawing Figures

FIGURE 2

FIGURE 3

COMPOSITION OF MATTER AND PROCESS

BACKGROUND OF THE INVENTION

The disclosed fermentation which produces antibiotic 354 also produces the known antibiotic gougerotin. This known antibiotic is described in the publication, JACS 94: 3272 (1972). Gougerotin was also known as aspiculamycin and is disclosed and claimed in U.S. Pat. No. 3,849,398.

BRIEF SUMMARY OF THE INVENTION

Antibiotic 354 is producible in a fermentation under controlled conditions using a biologically pure culture of the new microorganism *Streptomyces puniceus subsp. doliceus* NRRL 11160. Concomitantly produced with antibiotic 354 is the known antibiotic gougerotin. Antibiotic 354 is readily separated from gougerotin during the recovery procedure by subjecting a preparation containing the two antibiotics to absorption on a cellulose column followed by elution with methanol followed by water. Antibiotic 354 elutes with the methanol and gougerotin elutes with the water.

Antibiotic 354 is active against Gram-negative bacteria, and is especially very active against species of *Pseudomonas* and *Proteus*. For example, antibiotic 354 is active against *Pseudomonas aeruginosa* GN-315 (UC 6149) which is resistant to gentamycin, kanamycin and nalidixic acid. Thus, antibiotic 354 can be used to treat topical *Pseudomonas* infections resistant to gentamycin, kanamycin or nalidixic acid. It can also be used an an oil preservative, for example, as a bacteriostatic agent for inhibiting the growth of *Proteus vulgaris* which is known to cause spoilage in cutting oils. Also, it is useful in wash solutions for sanitation purposes, as in the washing of hands and the cleaning of equipment, floors, or furnishings of contaminated rooms or laboratories; it is also useful as an industrial preservative, for example, as a bacteriostatic rinse for laundered clothes and for impregnating paper and fabrics; and it is useful for suppressing the growth of sensitive organisms in plate assays and other microbiological media. It can also be used as a feed supplement to promote the growth of animals.

DETAILED DESCRIPTION OF THE INVENTION

Chemical and Physical Properties of Antibiotic 354:

Molecular Weight: 172 (field desorption mass. spec.)
Elemental Analysis: $(C_7H_9ClN_2O)_2 \cdot H_2SO_4$ (M.W. 474)
Found: C, 37.08; H, 4.79; N, 12.38; Cl, 15.52; S, 7.48; O, 22.75.

Figure 2:
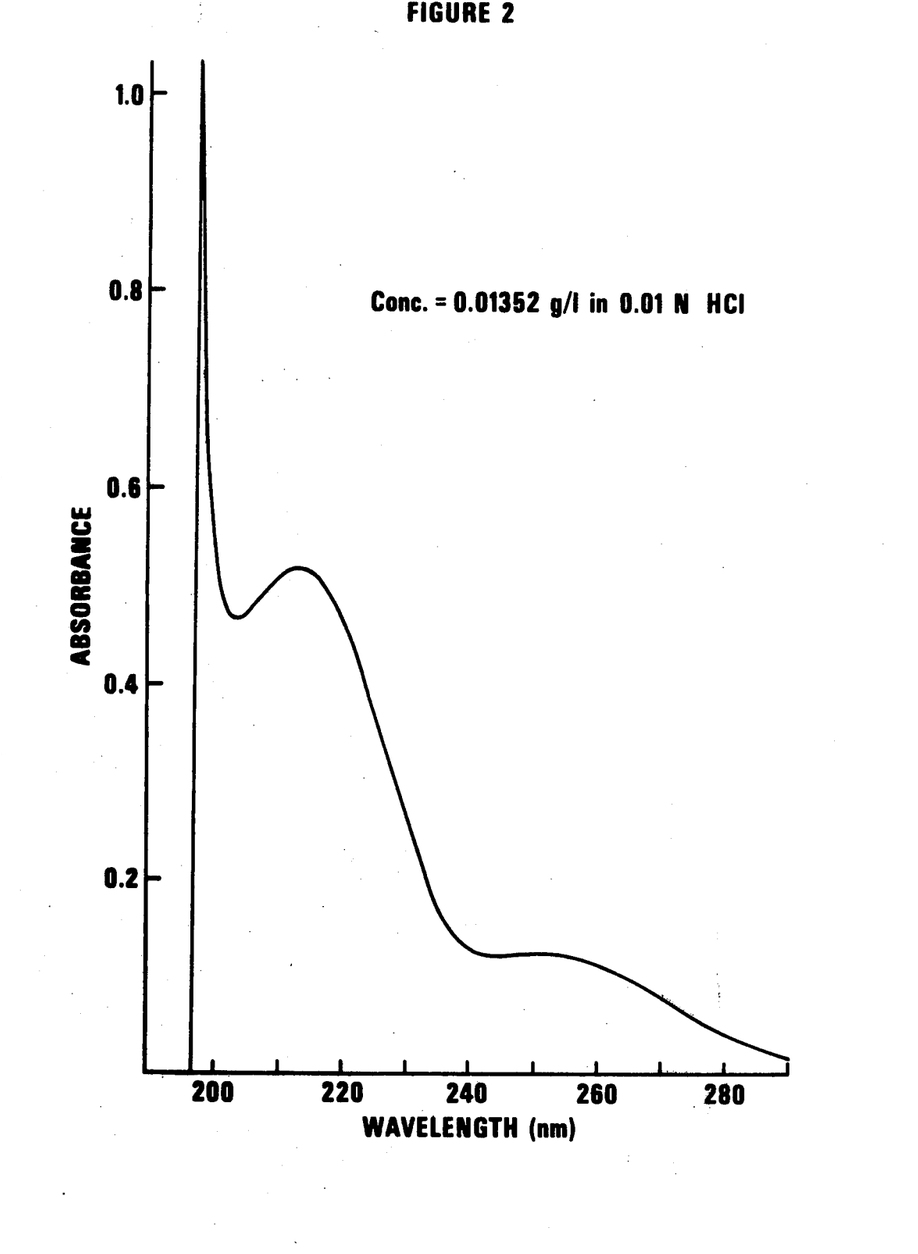

Ultraviolet Absorption Spectrum:

The ultraviolet absorption maxima of antibiotic 354, as reproduced in FIG. 2 of the drawings, are:

In 0.01 N HCl, λ, a, (E): 213 nm, 38.54, (6,650) and 251 nm, 9.02, (1,550).

Figure 1:
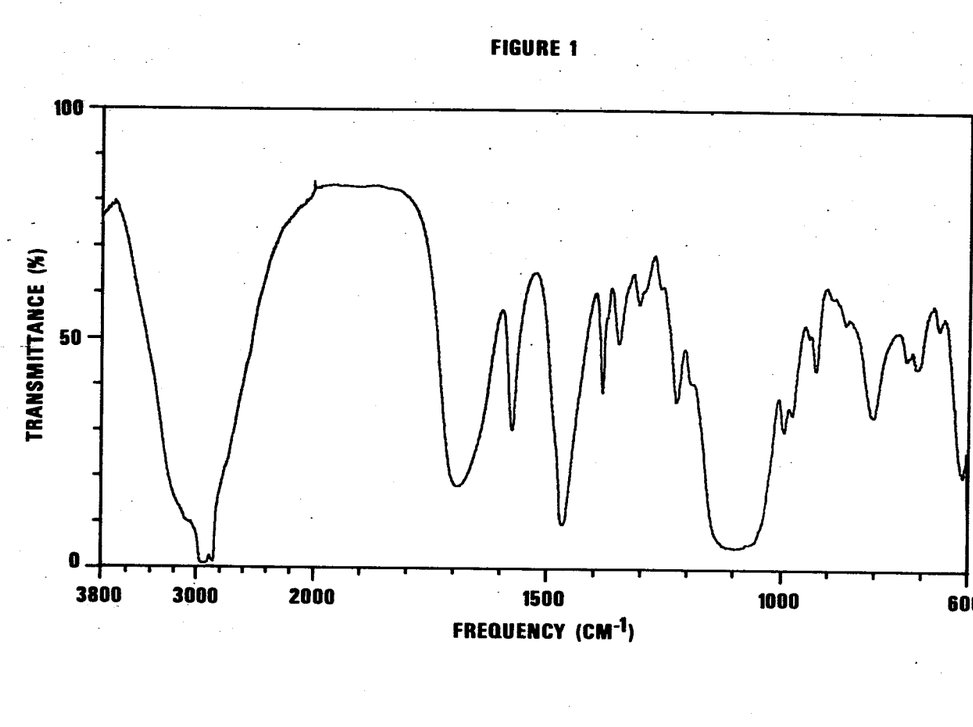

Infrared Absorption Spectrum:

Antibiotic 354, as the sulfate salt, has a characteristic infrared absorption spectrum in a mineral oil mull as shown in FIG. 1 of the drawings. Peaks are observed as the following wave lengths expressed in reciprocal centimeters.

Key: S = Strong  M = Medium  W = Weak  sh = shoulder

| Band Frequency (Wave Numbers) | Intensity |
|---|---|
| 3170 | S (sh) |
| 3070 | S |
| 2950 | S (oil) |
| 2920 | S (oil) |
| 2850 | S (oil) |
| 2750 | S (sh) |
| 1687 | S |
| 1572 | M |
| 1462 | S (oil) |
| 1377 | M (oil) |
| 1342 | M |
| 1300 | W |
| 1285 | W |
| 1252 | W |
| 1217 | M |
| 1187 | M |
| 1100 | S |
| 1062 | S (sh) |
| 992 | M |
| 975 | M |
| 940 | M |
| 925 | M |
| 890 | W |
| 862 | M |
| 800 | M |
| 730 | M |
| 705 | M |
| 660 | M |
| 608 | S |

Solubilities:

Antibiotic 354 is soluble in water, and poorly soluble in methanol, dimethylsulfoxide and dimethylformamide.

Figure 3:
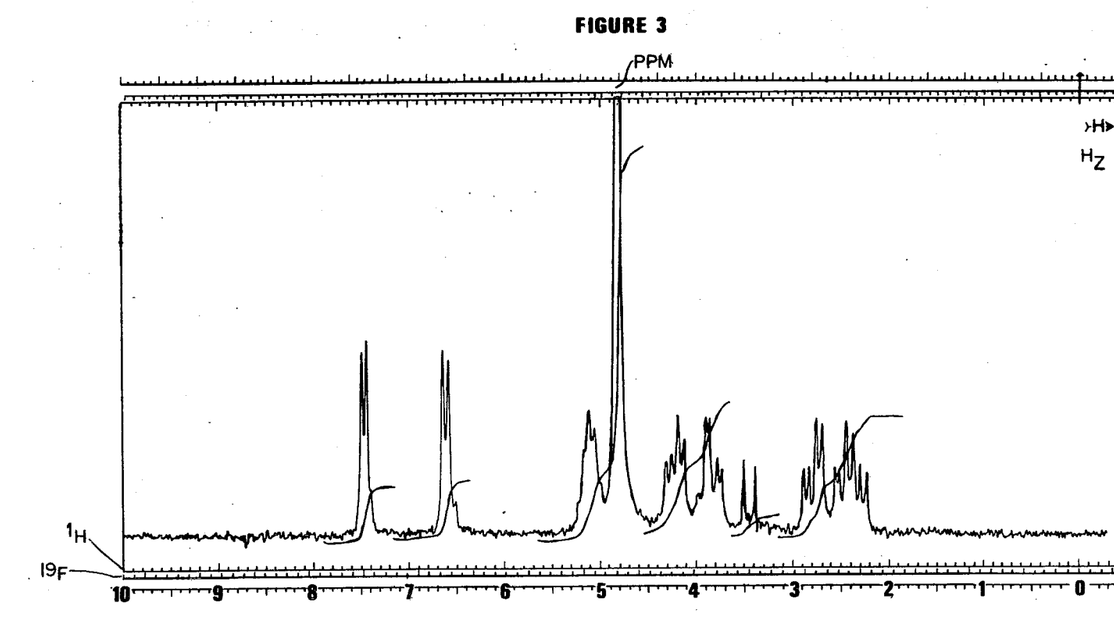

Nuclear Magnetic Resonance (NMR) Spectrum:

The 'H-NMR spectrum of antibiotic 354 (as the sulfate) at 60 megacycles is shown in FIG. 3 of the drawings. The NMR spectrum was observed on a Varian XL-100 Spectrometer on a solution (ca. 0.5 ml., ca. 15% concentration) of the sample of antibiotic 354 in deuterium oxide ($D_2O$). The spectrum was calibrated against external tetramethylsilane and the precision of $\Delta\gamma$ was $> +1$ c.p.s. Frequencies were recorded in c.p.s. downfield from tetramethylsilane.

Antibacterial Spectrum Of Antibiotic 354:

Antibiotic 354 shows the following zones of inhibition in millimeters (mm) on a standard disc plate assay (12.7 mm assay discs) at a concentration of 1 mg/ml.

| Microorganism | Zone Of Inhibition |
|---|---|
| *Bacillus subtillis* | 25 mm |
| *Pseudomonas mildenbergii* | 30 mm |

On testing antibiotic 354 by a microplate broth dilution assay using nutrient broth the following spectrum was observed.

| Microorganism | Minimum Inhibitory Concentration (mcg/ml) |
|---|---|
| *Staphylococcus aureus* UC 76 | 31.2 |
| *Streptococcus fecalis* UC 694 | 125 |
| *Escherichia coli* UC 45 | 15.6 |
| *Klebsiella pneumoniae* UC 57 | 31.2 |
| *Klebsiella pneumoniae* UC 58 | 7.8 |
| *Salmonella schottmuelleri* UC 126 | 7.8 |
| *Proteus vulgarius* UC 93 | 15.6 |
| *Proteus mirabilis* | 31.2 |
| *Pseudomonas aeruginosa* UC 95 | 15.6 |
| *Serratia marcescens* UC 131 | 3.9 |
| *Shigella flexneri* UC 143 | 15.6 |

| Microorganism | Minimum Inhibitory Concentration (mcg/ml) |
|---|---|
| *Salmonella typhi* | 15.6 |

"UC®" is a registered trademark of The Upjohn Company Culture Collection. These cultures can be obtained from The Upjohn Company in Kalamazoo, Michigan, upon request.

Antibiotic 354 has been shown to be active against *Pseudomonas aeruginosa* strains obtained from Bronson Hospital, Kalamazoo, Michigan. These strains were relatively resistant to the well-known antibiotics kanamycin, gentamycin, nalidixic acid, and Polymyxin B. The results of this comparative test, which was performed on a standard agar disc plate assay using 6.35 mm paper discs with 0.03 ml of antibiotic (1 mg/ml) per disc, follows.

| P. aeruginosa Strain No. | Zones of Inhibition (mm) | | | | |
|---|---|---|---|---|---|
| | Kanamycin | Gentamycin | Nalidixic Acid | Polymyxin B | Antibiotic 354 |
| 6429 | 11 | 14 | 13 | trace | 22 |
| 6430 | 11 | 14 | 13 | trace | 33 |
| 6431 | 0 | trace | 12 | trace | 22 |
| 6433 | trace | 11 | 13 | trace | 21 |
| 6434 | 13 | 22 | 13 | trace | 20 |
| 6435 | 0 | 13 | 17 | trace | 24 |
| 6436 | 0 | 9 | 13 | 9 | 22 |

Antibiotic 354 was also tested on a nutrient broth dilution test against the same *Pseudomonas* strains listed above. The test tubes were incubated at 32° C. for 18 hours. The results are as follows:

| P. aeruginosa Strain No. | Minimum Inhibitory Concentration (mcg/ml) |
|---|---|
| 6429 | 25 |
| 6430 | 25 |
| 6431 | 25 |
| 6433 | 25 |
| 6434 | 12.5 |
| 6435 | 12.5 |
| 6436 | 25 |

THE MICROORGANISM

The microorganism used for the production of antibiotic 354 and gougerotin is *Streptomyces puniceus* subsp. *doliceus,* NRRL 11160.

A subculture of this microorganism can be obtained from the permanent collection of the Northern Regional Research Laboratory, U.S. Department of Agriculture, Peoria, IL, U.S.A. Its accession number in this depository is NRRL 11160. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

An actinomycete, isolated from the Upjohn soils screens, was found to be similar in cultural characteristics to the cultures *Streptomyces griseus* var. purpureus, *S. californicus* and *S. vinaceus.* In 1955, Burkholder et al. [Burkholder, P. R. and S. H. Sun, L. E. Anderson, and J. Ehrlich. 1955. The identity of viomycin-producing cultures of *Streptomyces.* Bull. Torrey bot. Cl. 82:108–117], proposed that the viomycin-producing cultures be brought to synonymy in a new variety of *S. griseus* designated *S. griseus* var. purpureus. The viomycin-producers are distinguished from *S. griseus* by their distinctive red-purple reverse and pigment on many media [Buchanan, R. E., and N. E. Gibbons. 1974. Bergey's Manual of Determinative Bacteriology, 8th ed. The Williams and Wilkins Co., Baltimore] [Burkholder, P. R., supra] [Shirling, E. B., and D. Gottlieb. 1968. Cooperative description of type cultures of *Streptomyces.* II. Species descriptions from first study. Int. J. Syst. Bacteriol. 18:69-189] [Shirling, E. B., and D. Gottlieb. 1969. Cooperative description of type cultures of *Streptomyces. IV.* Species descriptions from the second, third and fourth studies. Int. J. Syst. Bacteriol. 19:391–512]. They do not differ from *S. griseus* [Shirling, E. B., and D. Gottlieb. 1968. Cooperative description of type cultures of *Streptomyces.* III. Additional species descriptions from first and second studies. Int. J. Syst. Bacteriol 18:280–399] in their temperature, carbon utilization, and general growth requirements, or in their spore chain or spore surface pattern.

In 1966, Buchanan et al. [Buchanan, R. E., J. G. Holt, and E. F. Lessel, Jr. 1966. Index Bergeyana. The Williams and Wilkins Co., Baltimore] declared S. griseus var purpureus Burkholder et al. an illegitimate name. S. vinaceus (Mayer et al.) Waks, of Henrici was also declared illegitimate. *S. californicus, S. floridae* and *S. puniceus* were considered legitimate names. In Bergey's Manual, 8th ed. [Buchanan, R. E., and N. E. Gibbons, supra], the last three named cultures are cited as type cultures. In Shirling and Gottlieb [Shirling and Gottlieb, supra at 18:69–189 and at 19:391–512], *S. californicus, S. puniceus* and *S. vinaceus* are cited as type cultures. The cultural characteristics cited in Burkholder, supra, in Shirling and Gottlieb, supra at 18:69–189, and in Bergey's Manual, 8th ed. [Buchanan, R. E., and N. E. Gibbons, supra] for *S. puniceus* are in agreement with the characteristics noted for the cultures compared with the new soil isolate. Of these cultures, *S. puniceus* Patelski (1950) is the earliest described [Burkholder, P. R., supra]. The new isolate exhibits minor differences in color of growth and antibiotic production from the cultures cited. On the basis of these differences, we propose the designation *Streptomyces puniceus* subsp. *doliceus* subsp. nov. for this new culture.

The methods used were those cited by Dietz [Dietz, A. 1954. Ektachrome transparencies as aids in actinomycete classification. Ann. N. Y. Acad. Sci. 60:152–154] [Dietz, A. 1967. *Streptomyces steffisburgensis* sp. n. J. Bacteriol. 94:2022–2026], Dietz and Mathews [Dietz A., and J. Mathews. 1971. Classification of *Streptomyces* spore surfaces into five groups. Appl. Microbiol. 21:527–533], and Shirling and Gottlieb [Shirling, E. B., and D. Gottlieb. 1966. Methods for characterization of *Streptomyces* species. Int. J. Syst. Bacteriol. 16: 313–340]. *S. puniceus* subsp. *doliceus* was compared with the following viomycin-producing cultures to which it appeared most similar on Ektachrome (Table 1): *S. griseus* var. purpureus NRRL 2423 (UC 2414), *S. griseus* var. purpureus CBS (UC 2468), *S. vinaceus* NRRL 2285 (UC 2920), and *S. californicus* ATCC 3312 (UC 5270).

Taxonomy. *Streptomyces puniceus* Finlay & Sobin subsp. doliceus Dietz and Li subsp. nov.

Color characteristics. Aerial growth cream to cream pink to lavender-pink. Melanin negative. Appearance on Ektachrome is given in Table 1. Reference color characteristics are given in Table 2. The new culture and *S. californicus* UC 5270 may be placed in the Gray and Violet color groups of Tresner and Backus [Tresner, H. D., and E. J. Backus. 1963. System of color wheels for streptomycete taxonomy. Appl. Microbiol. 11:335–338]; *S. griseus v. purpureus* UC 2414 in the Red and Violet color groups; and *S. griseus v. purpureus* UC 2468 and *S. vinaceus* UC 2920 in the Gray color group.

Microscopic characteristics. Spore chains long, flexuous (RF) in the sense of Pridham et al. [Pridham, T. G., C. W. Hesseltine, and R. G. Benedict. 1958. A guide for the classification of streptomycetes according to selected groups. Placement of strains in morphological sections. Appl. Microbiol. 6:52–79]. Spore chains may be in tufts. Spores, examined with the scanning electron microscope, are rectangular, appressed, and have a smooth surface which depresses to give a ridged effect.

Carbon utilization. See Tables 3 and 4.

Cultural and biochemical characteristics. See Table 5.

Temperature. All the cultures grew poorly at 18° C., well at 24° C. and very well at 28°–37° C. in 48 hours. There was no growth at 4° C., 45° C. or 55° C. Plates were removed from incubation after 14 days. Plates showing no growth were then incubated at 24° C. All plates from 4° C. showed growth in 24 hours at 24° C.; plates from 45° C. and 55° C. showed no growth with the exception of the plates containing the new culture. This culture grew out from the plates previously incubated at 45° C.

Antibiotic-producing properties. The reference cultures produce the antibiotic viomycin [Burkholder, P. R., supra]. UC 2414 produces the *Bacillus subtilis* and *Klebsiella pneumoniae* activities of the new culture. The new culture produces antibiotic gougerotin and antibiotic 354.

Table 1

| Agar Medium | Determination | *S. puniceus* subsp. *doliceus* NRRL 11160 | *S. griseus* var. *purpureus* NRRL 2423 | *S. griseus* var. *purpureus* UC 2468 | *S. vinaceus* NRRL 2285 | *S. californicus* ATCC 3312 |
|---|---|---|---|---|---|---|
| Bennett's | S | Lavender-pink | Lavender-pink | Lavender-pink | Lavender-pink | Trace lavender-pink |
| | R | Red-tan | Red-tan | Red-tan | Red-tan | Red-tan |
| Czapek's sucrose | S | Pale pink | Pink | Pink | Pale pink | Very slight trace pink |
| | R | Pale pink | Pink | Pale pink | Pale pink | Pale pink |
| Maltose tryptone | S | Lavender-pink | Lavender-pink | Lavender-pink | Lavender-pink | Very pale pink |
| | R | Red-tan | Red-tan | Red-tan | Red-tan | Yellow-tan |
| Peptone-iron | S | — | Trace lavender-pink | Trace lavender-pink | Trace lavender-pink | |
| | R | Yellow-tan | Yellow-tan | Yellow-tan | Yellow-tan | Yellow-tan |
| 0.1% Tyrosine | S | Pale pink | Pale pink | Pale pink | Pale pink | Trace pale pink |
| | R | Yellow-tan | Red-tan | Pale pink | Pale pink | Red-tan |
| Casein starch | S | Lavender-pink | Lavender-pink | Lavender-pink | Lavender-pink | Very slight trace pink |
| | R | Gray-tan | Gray-tan | Gray-tan | Gray-tan | Gray-tan |

S = Surface
R = Reverse
*Dietz, A. 1954. Ektachrome transparencies as aids in actinomycete classification. Ann. N.Y. Acad. Sci. 60:152–154.

Table 2.

Reference Color Characteristics from ISCC-NBS Color Name Charts Illustrated with Centroid Colors*

| Agar Medium | Determination | *S. puniceus* subsp. *doliceus* NRRL 11160 Chip No. | Color | *S. griseus* var. *purpureus* NRRL 2423 Chip No. | Color | *S. griseus* var. *purpureus* UC 2468 Chip No. | Color | *S. vinaceus* NRRL 2285 Chip No. | Color | *S. californicus* ATCC 3312 Chip No. | Color |
|---|---|---|---|---|---|---|---|---|---|---|---|
| Bennett's | S | 240 | Light reddish purple to | 32 | Grayish yellowish pink | 63 | Light brownish gray | 63 | Light brownish gray | 229 | Dark grayish purple |
| | | 93 | Yellowish gray | | | | | | | | |
| | R | 17 | Very dark red | 21 | Blackish red | 19 | Grayish red | 20 | Dark grayish red | 260 | Very dark purplish red |
| | P | 57 | Light brown | 45 | Light grayish reddish brown | Pale | Light grayish brown | 60 | Light grayish brown | 60 | Light grayish brown |
| Czapek's sucrose | S | 253 | Grayish purplish pink | 253 | Grayish purplish pink | 93 | Yellowish gray | 93 | Yellowish gray | 223 | Moderate purple |
| | R | 253 | Grayish purplish pink | 237 | Strong reddish purple | 93 | Yellowish gray | 244 | Pale reddish purple | 223 | Moderate purple |
| | P | — | — | — | — | — | — | — | — | — | — |
| Maltose tryptone | S | 226 | Very pale purple | 32 | Grayish yellowish | 93 | Yellowish gray | 93 | Yellowish gray | 228 | Grayish purple |
| | R | 21 | Blackish red | 17 | Very dark red | 62 | Dark grayish brown | 81 | Dark grayish yellowish brown | 257 | Very deep purplish red |
| | P | 57 | Light brown | 45 | Light grayish reddish brown | 60 | Light grayish brown | 60 | Light grayish brown | — | — |
| Hickey-Tresner | S | 63 | Light brownish | 32 | Grayish yellowish | 93 | Yellowish gray | 93 | Yellowish gray | 227 | Pale purple |

Table 2.-continued

Reference Color Characteristics from ISCC-NBS Color Name Charts Illustrated with Centroid Colors*

| Agar Medium | Determination | S. puniceus subsp. doliceus NRRL 11160 Chip No. | Color | S. griseus var. purpureus NRRL 2423 Chip No. | Color | S. griseus var. purpureus UC 2468 Chip No. | Color | S. vinaceus NRRL 2285 Chip No. | Color | S. californicus ATCC 3312 Chip No. | Color |
|---|---|---|---|---|---|---|---|---|---|---|---|
| | R | 17 | gray Very dark red | 260 | pink Very dark purplish red | 259 | Dark purplish red | 20 | Dark grayish red | 260 | Very dark purplish red |
| | P | 57 | Light brown | 45 | Light grayish reddish brown | 60 | Light grayish brown | 60 | Light grayish brown | 60 | Light grayish brown |
| Yeast extract-malt extract (ISP-2) | S | 63 | Light brownish gray | 32 | Grayish yellowish pink | 93 | Yellowish gray | 93 | Yellowish gray | 234 | Dark purplish gray |
| | R | 73 | Pale orange yellow to | 73 | Pale orange yellow to | 73 | Pale orange yellow to | 73 | Pale orange yellow to | 17 | Very dark red |
| | | 21 | Blackish red | 46 | Grayish reddish brown | 46 | Grayish reddish brown | 20 | Dark grayish red | — | — |
| | P | 57 | Light brown | 45 | Light grayish reddish brown | 60 | Light grayish brown | 60 | Light grayish brown | — | — |
| Oatmeal (ISP-3) | S | 240 | Light reddish purple to | 226 | Very pale purple | 63 | Light brownish gray | 93 | Yellowish gray | 257 | Very deep purplish red |
| | | 93 | Yellowish gray | | | | | | | | |
| | R | 242 | Dark reddish purple | 259 | Dark purplish red | 259 | Dark purplish red | 262 | Grayish purplish red | 17 | Very dark red |
| | P | 57 | Light brown | 45 | Light grayish reddish brown | 60 | Light grayish brown | 60 | Light grayish brown | 60 | Light grayish brown |
| Inorganic-salts starch (ISP-4) | S | 63 | Light brownish gray | 32 | Grayish yellowish pink | 93 | Yellowish gray | 93 | Yellowish gray | 227 | Pale purple |
| | R | 242 | Dark reddish purple | 257 | Very deep purplish red | 257 | Very deep purplish red | 259 | Dark Purplish red | 21 | Blackish red |
| | P | 57 | Light brown | 45 | Light grayish reddish brown | 60 | Light grayish brown | 60 | Light grayish brown | 60 | Light grayish brown |
| Glycerol-asparagine (ISP-5) | S | 63 | Light brownish gray | 32 | Grayish yellowish pink | 93 | Yellowish gray | 93 | Yellowish gray | 227 | Pale purple |
| | R | 21 | Blackish red | 257 | Very deep purplish red | 257 | Very deep purplish red | 259 | Dark purplish red | 21 | Blackish red |
| | P | 57 | Light brown | 45 | Light grayish reddish brown | 60 | Light grayish brown | 60 | Light grayish brown | 60 | Light grayish brown |

S = Surface  R = Reverse  P = Pigment
*Kelly, K. L., and D. B. Judd. 1955. The ISCC-NBS method of designating colors and a dictionary of color names. U.S. Dept. of Comm. Circ. 553, Washington, D.C.

Table 3

Growth on Carbon in the Synthetic Medium of Pridham and Gottlieb *

| | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
|---|---|---|---|---|---|
| CONTROL | (+) | (+) | (−) | (+) | (−) |
| 1. D-Xylose | + | + | + | + | + |
| 2. L-Arabinose | (+) | (+) | (+) | (+) | (+) |
| 3. Rhamnose | (+) | (+) | − | (+) | − |
| 4. D-Fructose | + | + | + | + | + |
| 5. D-Galactose | + | + | + | + | + |
| 6. D-Glucose | + | + | + | + | + |
| 7. D-Mannose | + | + | + | + | + |
| 8. Maltose | + | + | + | + | (+) |
| 9. Sucrose | (+) | (+) | (+) | (+) | (+) |
| 10. Lactose | (+) | (+) | (−) | (+) | + |
| 11. Cellobiose | + | + | + | + | + |
| 12. Raffinose | (+) | (+) | (+) | (+) | (−) |
| 13. Dextrin | + | + | + | + | + |
| 14. Inulin | (+) | (+) | (+) | (+) | (−) |
| 15. Soluble Starch | + | + | + | + | + |

Table 3-continued

| | Growth on Carbon in the Synthetic Medium of Pridham and Gottlieb * | | | | |
|---|---|---|---|---|---|
| | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
| 16. Glycerol | + | + | + | + | + |
| 17. Dulcitol | (+) | (+) | (−) | (+) | (−) |
| 18. D-Mannitol | + | + | + | + | + |
| 19. D-Sorbitol | (+) | (+) | (+) | (+) | (−) |
| 20. Inositol | (+) | (+) | (+) | (+) | (−) |
| 21. Salicin | (+) | (+) | (+) | (+) | (+) |
| 22. Phenol | − | − | − | − | − |
| 23. Cresol | − | − | − | − | − |
| 24. Na Formate | (−) | (−) | (−) | − | − |
| 25. Na Oxalate | (−) | (+) | (+) | (+) | − |
| 26. Na Tartrate | (+) | (+) | (−) | (+) | (−) |
| 27. Na Salicylate | − | − | − | − | − |
| 28. Na Acetate | + | + | + | + | (+)→+ |
| 29. Na Citrate | + | + | + | + | (−) |
| 30. Na Succinate | + | + | + | + | (+) |

+ = Good growth
(+) = Fair growth
(−) = Trace growth
− = No growth
* Pridham, T.G., and Gottlieb. 1948. The utilization of carbon compounds by some Actinomycetales as an aid for species determination. J. Bacteriol. 56:107–114.

Table 4

| | Growth on Carbon Compounds in the Synthetic Medium of Shirling and Gottlieb * | | | | |
|---|---|---|---|---|---|
| | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
| Negative Control (Synthetic Medium-ISP-9) | ± | ± | ± | ± | − |
| Positive Control (Synthetic Medium + D-Glucose | ++ | ++ | ++ | ++ | ++ |
| Carbon Compounds: | | | | | |
| L-Arabinose | ± | + | + | ± | + |
| Sucrose | − | − | ± | − | − |
| D-Xylose | ++ | ++ | + | + | ++ |
| Inositol | − | − | − | − | − |
| D-Mannitol | ++ | ++ | ++ | ++ | ++ |
| D-Fructose | + | ++ | + | ++ | ++ |
| Rhamnose | ± | ± | ± | ± | ± |
| Raffinose | − | − | − | − | − |
| Cellulose | − | − | − | − | − |

++ Strong utilization
+ Positive utilization
± Doubtful utilization
− Negative utilizationL6 * Shirling, E.B., and D. Gottlieb. 1966. Methods for characterization of Streptomyces species. Int. J. Syst. Bacteriol. 16:313–340.

Table 5

| | | Cultural and Biochemical Characteristics | | | | |
|---|---|---|---|---|---|---|
| Medium | Determination | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
| Agar | | | | | | |
| Peptone-iron | S | Cream-pink | Pale cream-pink | Cream | Pale Cream pink | Trace cream |
| | R | Yellow-tan | Yellow-tan | Yellow-tan | Yellow-tan | Yellow-tan |
| | P | — | — | — | — | — |
| | O | Melanin negative | Melanin negative | Melanin negative | Melanin negative | Melanin negative |
| Calcium malate | S | Very slight trace cream-pink | Cream | Trace cream | Cream | Trace cream aerial |
| | R | Colorless | Colorless | Colorless | Colorless | Colorless |
| | P | — | — | — | — | — |
| | O | Malate not solubilized | Malate not solublized | Malate not solubilized | Malate not solublized | Malate not solubilized |
| Glucose asparagine | S | Cream-pink | Cream | Cream | Cream | Cream-pink |
| | R | Maroon center, tan edge | Maroon center, tan edge | Pale pink-red center, cream edge | Pale pink-red center, cream edge | Maroon center, tan edge |
| | P | Pale pink | Pale pink | Pale pink | Pale pink | Pale pink |
| Skim milk | S | Very slight trace cream-pink | Cream | Cream | Cream-pink | — |
| | R | Yellow-tan- | Yellow-tan- | Yellow-tan- | Yellow-tan- | Yellow-tan- |

Table 5-continued

Cultural and Biochemical Characteristics

| Medium | Determination | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
|---|---|---|---|---|---|---|
| | P | orange Yellow-tan-orange | orange Yellow-tan-orange | orange Yellow-tan-orange | orange Yellow-tan-orange | orange Yellow-tan-orange |
| | O | Casein solublized | Casein solublized | Casein solublized | Casein solublized | Casein solublized |
| Tyrosine | S | Cream | Cream | Cream | Cream | Trace cream |
| | R | Light tan | Tan | Tan | Tan | Pale yellow |
| | P | Tan | Tan | Tan | Tan | Pale yellow |
| | O | Tyrosine solublized | Tyrosine solublized | Tyrosine solublized | Tyrosine solublized | Tyrosine solublized |
| Xanthine | S | Cream | Cream | Cream | Cream | Trace cream |
| | R | Pale cream-tan | Cream-yellow | Cream-yellow | Cream-yellow | Pale yellow |
| | P | Cream-tan to very pale tan | Cream-yellow to pale tan | Cream-yellow to pale tan | Cream-yellow to pale tan | Very pale yellow |
| | O | Xanthine not solublized | Xanthine not solublized | Xanthine slightly solublized | Xanthine not solublized | Xanthine solublized |
| Nutrient starch | S | Cream | Cream | Cream | Cream | Trace cream |
| | R | Pale cream-tan | Cream-yellow | Pale cream-pink-tan | Pale cream-pink-tan | Very pale yellow |
| | P | None to very pale tan | Cream-yellow to very pale tan | Very pale pink-tan | pink-tan | — |
| | O | Starch solublized | Starch solublized | Starch solublized | Starch solublized | Starch solublized |
| Yeast extract-malt extract | S | Pale lavender with cream edge | Pale lavender with cream edge | Craem with fish-net edge | Cream with fish-net edge | Trace cream |
| | R | Maroon with tan edge | Maroon with tan edge | Maroon with tan edge | Maroon with tan edge | Pale reddish-tan |
| | P | Pale red-tan | Pale red-tan | Very pale tan | Very pale tan | Very pale red-tan |
| Peptone-yeast extract-iron (ISP-6) | S | Colorless vegetative | Trace cream aerial on colorless vegetative | White | White | Colorless vegetative |
| | R | Colorless | Colorless | Yellow-tan | Yellow-tan | Yellow-tan |
| | P | Trace tan | Trace tan | Yellow-tan | Yellow-tan | Yellow-tan |
| | O | Melanin negative | Melanin negative | Melanin negative | Melanin negative | Melanin negative |
| Tyrosine (ISP-7) | S | Mottled cream-lavender | Cream | Gray-cream | Gray-cream | Lavender |
| | R | Maroon | Maroon | Maroon | Maroon | Maroon |
| | P | Trace pale red-tan | Trace pale red-tan | Gray-pink | Gray-pink | Pale red-pink |
| | O | Melanin negative | Melanin negative | Melanin negative | Melanin negative | Melanin negative |
| Gelatin | | | | | | |
| Plain | S | Trace white aerial | Trace white aerial | Trace colorless vegetative | Trace white aerial | — |
| | P | Pale yellow | Pale yellow | Pale yellow | Pale yellow | Pale yellow |
| | O | Liquefaction ½ | Liquefaction ½ | Liquefaction ½ | Liquefaction ½ | No liquefaction |
| Nutrient | S | Trace white aerial | Trace white aerial | Trace white aerial | Trace white aerial | — |
| | P | Yellow | Yellow | Yellow | Yellow | Yellow |
| | O | Liquefaction ½ | Liquefaction ½ | Liquefaction ½ | Liquefaction ½ | No liquefaction |
| Nitrate Broth | | | | | | |
| Synthetic | S | — | — | — | Cream-pink aerial on lavender-pink vegetative pellicle | — |
| | P | — | — | — | — | — |
| | O | Compact bottom growth No reduction Red with Zn dust | Trace bottom growth No reduction Red with Zn dust | Compact bottom growth No reduction Red with Zn dust | Trace bottom growth Reduction | Compact bottom growth No reduction Red with Zn dust |
| Nutrient | S | Cream aerial on maroon ring | Lavender aerial on surface pellicle | Lavender aerial on surface pellicle | Gray-cream aerial on maroon ring | Gray-cream aerial on maroon ring |
| | P | — | — | — | — | — |
| | O | Trace bottom growth No reduction Red with Zn dust | Trace bottom growth Reduction | Trace bottom growth Reduction | Trace bottom growth Reduction | Trace bottom growth Reduction |
| Litmus Milk | S | Cream aerial on blue vegetative | Gray aerial on blue vegetative | Gray aerial on blue-gray ring | Gray aerial on blue-gray ring | Trace gray aerial on blue-gray |

Table 5-continued

| Medium | Determination | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
|---|---|---|---|---|---|---|
| | P | ring Slight purple | ring Slight purple | — | — | red ring — |
| | O | Trace peptonization | Trace peptonization | Peptonization | Peptonization | Peptonization good Litmus reduced in one |
| | | pH 7.07 | pH 7.12 | pH 7.3 | pH 7.07 | pH 7.07 |

S = Surface
R = Reverse
P = Pigment
O = Other characteristics

The compounds of the invention process are produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compounds by the invention process can be effected at any temperature conducive to satisfactory growth of the microorganism, for example, between about 18° and 40° C., and preferably between about 20° and 28° C. Ordinarily, optimum production of the compounds is obtained. in about 3 to 15 days. The medium normally remains acidic during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compounds and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compounds, so long as a good growth of the microorganism is obtained.

A variety of procedures can be employed in the isolation and purification of the compounds produced by the subject invention from fermentation beers, for example, charcoal absorption, 1-butanol extraction, and adsorption on cellulose and cation exchange resins.

In a preferred recovery process the compounds produced by the subject process invention are recovered from the culture medium by separation of the mycelia and undissolved solids by conventional means, such as by filtration or centrifugation.

The antibiotics are then recovered from the filtered or centrifuged broth by absorption on a charcoal column. The charcoal can be eluted by passing 10 to 50% acetone in water (v/v) to remove the antibiotics.

The eluates are pooled and concentrated to an aqueous solution. This solution then is passed over a weak cation exchange resin in the ammonium form, for example, IRC-50 which is supplied by Rohm & Haas, Philadelphia, Pennsylvania. The resin can be eluted with an inorganic salt, for example, ammonium chloride, ammonium sulfate (preferred), calcium perchlorate, and the like. Collected fractions are assayed for antibacterial activity as herein described. Fractions showing antibacterial activity can be extracted with 1-butanol to remove impurities. The antibiotics remain in the aqueous phase.

The aqueous phase can be passed over a charcoal column which is then eluted with 25% acetone in water (v/v) and fractions are collected. These fractions are concentrated to an aqueous which is then lyophilized. The next step of the purification process will separate antibiotic 354 from gougerotin.

The lyophilized solid containing antibiotic 354 and gougerotin, described above, is dissolved in a minimum amount of water. This material is injected or layered onto a cellulose column. The column is eluted with methanol and fractions are collected. These fractions contain antibiotic 354. Gougerotin is removed from the cellulose column by eluting the column with water.

Antibiotic 354 is obtained in essentially pure form from the above-described methanol eluates by first concentrating the pooled eluates to a solid and then passing the solid, which has been dissolved in a minimum amount of water, over a strong cation exchange resin, for example, Dowex 50 (supplied by Dow Chemical Co., Midland, Michigan). The column is eluted with a solution of an inorganic salt (ammonium sulfate preferred) and fractions containing essentially pure antibiotic 354 are collected.

Essentially pure gougerotin can be obtained by taking the fractions containing gougerotin from the cellulose column, described above, and passing them over a strong cation exchange resin, as described above for antibiotic 354.

Since antibiotic 354 is a strongly basic compound, procedures involving adsorption on cationic ion exchange resins and elution by organic bases or ammonia can be used to purify crude preparations of antibiotic 354. Also, crude preparations of antibiotic 354 can be purified by transformation to a salt form by treatment with inorganic or organic acids. The base form of the antibiotic can be recovered by neutralization of the acid anion with ammonia or other inorganic or organic bases.

In order to make salts of antibiotic 354 with both inorganic or organic acids, as hereinafter disclosed in exemplary form, it is necessary that the acid be carefully added to an aqueous solution of antibiotic 354 in view of the instability of this antibiotic at acid pH's. Examples of inorganic and organic acids which can be used, but which examples should not be considered limiting, are hydrochloric, sulfuric, phosphoric, acetic, succinic, citric, lactic, maleic, fumaric, pamoic, cholic, palmitic, mucic, camphoric, glutaric, glycolic, phthalic, tartaric, lauric, stearic, salicyclic, 3-phenylsalicyclic, 5-phenylsalicyclic, 3-methylglutaric, orthiosulfobenzoic, cyclohexanesulfamic, cyclopentanepropionic, 1,2-cyclohexanedicarboxylic, 4-cyclohexenecarboxylic, octadecenylsuccinic, octenylsuccinic, methanesulfonic, benzenesulfonic, helianthic, Reinecke's, dimethyldithiocarbamic, sorbic, monochloroacetic, undecylenic, 4'-hydroxyazobenzene-4-sulfonic, octadecylsulfuric, picric, benzoic, cinnamic, and like acids.

Other procedures for making certain salts are as follows. The sulfate salts can be made by using ammonium sulfate elution from a cation exchange resin. Also, the acetate salts can be made by using pyridinium acetate to elute the antibiotic from cation exchange resins. Further, the chloride salts of antibiotic 354 can be made by using ammonium chloride to elute the antibiotic from a cation exchange resin. The sulfate salts can be converted to the chloride by passing them over an anion exchange resin, for example, Dowex 1 (Cl$^-$) and Dowex 2 (Cl$^-$). If the resin is used in the OH$^-$ form, the free base of 354 is isolated.

The salts of antibiotic 354 can be used for the same biological purposes as the parent antibiotic.

Acylates of antibiotic 354 can be made as follows: A sample of antibiotic 354 is dissolved in an excess of a silylating reagent such as TMS-imidazole or bis-TMS-trifluoroacetamide. A catalyst such as trimethylchlorosilane and/or a base such as pyridine may be used but neither is necessary. An acylating reagent such as trifluoroacetylimidazole or acetic anhydride is then added. Acylation is rapid and quantitative as judged by combined gas chromatography-mass spectroscopy. The peaks corresponding to silylated antibiotic 354 (both mono and di-silylated derivatives can be present) disappear and a new one appears with longer retention time and with a mass spectrum indicative of an acylated and monosilylated antibiotic 354. This derivative can then be selectively hydrolyzed with methanol or water to give an acylated derivative of antibiotic 354.

Suitable acid-binding agents include amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and loweralkoxyhydrocarboncarboxylic acids include hydrocarboncarboxylic acids as given above which are substituted by one or more of halogen, nitro, hydroxy, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarboncarboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methylcyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;

ethoxyformic acid (ethyl hydrogen carbonate); and the like.

The above acylates of antibiotic 354 are useful to upgrade the parent compound, i.e. by acylating the parent compound, then removing the acyl group, the parent compound is isolated in a purer form.

Trimethylsilylation of antibiotic 354 gives a volatile di-TMS derivative (along with a little mono-TMS derivative) which is useful in vapor phase chromatography and mass spectroscopy work. This derivative can be prepared by heating a sample of antibiotic 354 at about 60° C. for about 30 minutes in tetrahydrofuran with an excess of bistrimethylsilylacetamide.

Also, the mono-TMS derivative can be prepared using either trimethylsilylimidazole or bistrimethylsilyltrifluoroacetamide. The monosilylated antibiotic 354 can be acylated in situ using trifluoroacetylimidazole, trifluoroacetic anhydride or acetic anhydride. These are also useful in vpc-mass spectroscopic work and represent a practical route to selective (O vs. N) protection of antibiotic 354.

The following illustrate the use in formulations of the compositions of the present invention. All percentages are by weight and all solvent mixture proportions are by volume unless otherwise noted.

The compositions of the present invention are preferably presented for administration to humans and animals in unit dosage forms, such as tablets, capsules, powders, granules, sterile parenteral solutions or suspensions, and oral solutions or suspensions, containing suitable quantities of antibiotic 354 or its pharmacologically acceptable salts.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, starch, lactose, acacia, methylcellulose, and functionally similar materials as pharmaceutical diluents or carriers. In their simplest embodiment, capsules, like tablets, are prepared by mixing the antibiotic with an inert pharmaceutical diluent and filling the mixture into a hard gelatin capsule of appropriate size. Soft gelatin capsules are prepared by machine encapsulation of a slurry of the antibiotic with corn oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar, saccharin, and cyclamate together with an aromatic flavoring agent. Suspensions can be prepared of the insoluble forms with a syrup vehicle with the aid of a suspending agent such as acacia, tragacanth, methylcellulose and the like.

Topical ointments can be prepared by dispersing the antibiotic in a suitable ointment base such as petrolatum, lanolin, polyethylene glycols, mixtures thereof, and the like. Advantageously, the antibiotic is finely divided by means of a colloid mill utilizing light liquid petrolatum as a levigating agent prior to dispersing in the ointment base. Topical creams and lotions are prepared by dispersing the antibiotic in the oil phase prior to the emulsification of the oil phase in water.

For parenteral administration, fluid unit dosage forms are prepared utilizing the antibiotic and a sterile vehicle, water being preferred. The antibiotic, depending on the form and concentration used, can be either suspended or dissolved in the vehicle. In preparing solutions the water-soluble antibiotic can be dissolved in water for injection and filter sterilized before filling into a suitable vial or ampule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the powder prior to use. Parenteral suspensions are prepared in substantially the same manner except that the antibiotic is suspended in the vehicle instead of being dissolved and sterilization cannot be accomplished by filtration. The antibiotic can be sterilized by exposure to ethylene oxide before suspending in the sterile vehicle. Advantageously, a surfactant or wetting agent is included in the composition to facilitate uniform distribution of the antibiotic.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, troches, suppositories, powder packets, granules, wafers, cachets, teaspoonfuls, tablespoonfuls, dropperfuls, ampuls, vials, segregated multiples of any of the foregoing, and other forms as herein described.

The dosage of antibiotic 354 for treatment depends on route of administration; the age, weight, and condition of the patent; and the particular disease to be treated. For adults, a dosage schedule of from about 50 to 500 mg, 1 to 4 times daily (every 6 hours), embraces the effective range for the treatment of most conditions. For severe conditions, 4 gm or more a day can be used in divided doses. For infants the dosage is calculated on the basis of 15 mg/kg by weight, and for children 15 to 25 mg/kg, to be administered every 6 hours.

Antibiotic 354 is compounded with a suitable pharmaceutical carrier in unit dosage form for convenient and effective administration. In the preferred embodiments of this invention, the dosage units contain antibiotic 354 in 25, 50, 100, 200, and 500 mg amounts for systemic treatment; in 0.25, 0.5, 1 and 5 percent amounts for topical or localized treatment and 5 to 65 percent w/v for parenteral preparations. The dosage of compositions containing antibiotic 354 and one or more other active ingredients is to be determined with reference to the usual dosage of each such ingredient. A dose of from about 1 mg/kg/day to about 60 mg/kg/day is preferred for systemic treatment.

The following examples are illustrative of the process and products of the invention, but are not to be construed as limiting. All percentages are by weight and all solvent mixture proportions are by volume unless otherwise noted.

EXAMPLE 1

A. Fermentation

A biologically pure culture of Streptomyces puniceus subsp. doliceus, NRRL 11160, is used to inoculate 500-ml Erlenmeyer seed flasks containing 100 ml of sterile medium consisting of the following ingredients:

| Glucose | 10 | g/l |
|---|---|---|
| Yeast Extract | 2.5 | g/l |
| Peptone | 10 | g/l |
| Deionized Water q.s. | 1 | liter |

The seed medium presterilization pH is 6.5. The seed inoculum is grown for three days at 28° C. on a Gump rotary shaker operating at 250 r.p.m. Seed inoculum, prepared as described above, is used to inoculate 500-ml Erlenmeyer fermentation flasks containing 100 ml of sterile fermentation medium consisting of the following ingredients:

| Brer Rabbit/Sucrest* | 20 | ml/l |
|---|---|---|
| Yeast Extract/Brewer's Yeast** | 2 | g/l |
| Dextrin*** | 10 | g/l |
| Cerelose*** | 15 | g/l |
| Proteose-Peptone #3** | 10 | g/l |
| Peanut Meal | 5 | g/l |
| Water q.s. | 1 | liter |

*RJR Foods, Inc., New York, NY
**Difco Laboratories, Detroit, MI
***CPC International, Inc., Englewood Cliffs, NJ The presterilization pH is 7.0. The fermentation flasks are inoculated at the rate of 5 ml of seed inoculum per 100 ml of fermentation medium. The fermentation flasks are grown for 3 days at a temperature of 25°–28° C. on a Gump rotary shaker operating at 250 r.p.m.

A representative shake flask fermentation harvested after 3 days shows the following assay pattern against *Pseudomonas mildenbergii* (UC 3029).

| Day | Assay Results (BU/ml) |
|---|---|
| 1 | 0 |
| 2 | 14 |
| 3 | 14 |

The assay is an agar disc plate assay using the microorganism *P. mildenbergii*. The agar medium is buffered with 0.1 M phosphate buffer at a pH of 7.4. A unit volume (0.08 ml) of solution containing the substance to be assayed is placed on a 12.7 mm paper disc which is then placed on an agar plate seeded with the assay organism. The agar plate is then incubated for 16–18 hours at 37° C. A biounit (BU) is defined as the concentration of the antibiotic which gives a 20 mm zone of inhibition under the above assay conditions. Thus, if for example a fermentation beer, or other solution containing the antibiotic, needs to be diluted 1/100 to give a 20 mm zone of inhibition, the potency of such beer or solution is 100 BU per ml.

B. Recovery

(1) Carbon Sorption

Ten liters of shake flask-grown beer, as described above, is stirred with 4 l washed, granular charcoal for 15 minutes. The charcoal is allowed to settle for 10 minutes and the beer is decanted. The charcoal is washed with deionized water until the water remains clear. An overhead paddle stirrer is used in the first step and a 10 l pail in the second step. The charcoal is slurried into a chromatography tube with deionized water. The activities are eluted with 25% acetone in water using gravity flow at the highest possible flow rate. One liter fractions are collected until a yellow color emerges. When the yellow color is almost undetectable small fractions are again collected. The yellow fractions (11 l) are concentrated to an aqueous at 35°–40° C./1 mm and assayed. The data are presented in Table I below. It is seen that 80% of the UC 3029 biounits are recovered from the column.

Table 1

| Sample | Volume | Dilution | Pseudomonas mildenbergii (UC 3029) | Bacillus subtilis | Conc. | BU/mg |
|---|---|---|---|---|---|---|
| Whole Beer | 10 l | FS * | 28 mm | 24 mm | — | — |
|  |  | 1:2 | 23 | 21 | — | — |
|  |  | 1:4 | trace | 20 | — | — |
|  |  | 1:8 | NZ ** | 19 | — | — |
| Spent Beer | 11 l | FS | NZ | 20 | — | — |
| 1st Eluate | 3 l | FS | NZ | — | — | — |
| 2nd Eluate | 9 l | FS | 25 | — | — | — |
| 3rd Eluate | 2 l | FS | NZ | — | — | — |
| Aqueous Pool | 8 l | FS | 29 | 23 | 16.9 mg/ml | 0.18 |
|  |  | 1:2 | 23 | 19 | (3 BU/ml) |  |
|  |  | 1:4 | 16 | trace |  |  |

FS * = Full strength
NZ ** = NO Zone

(2) IRC-50 Sorption

Carbon eluates from four runs (about 48 l of beer in all), as described above, are pooled to give 33 l of aqueous which assay for a total of 91,000 UC 3029 biounits. This is passed over 2 pounds of IRC-50 (NH$_4^+$) in a chromatography tube at 5–6 l/hour. The column is then washed with 4 l of deionized water and eluted with 1 M (NH$_4$)$_2$SO$_4$ solution. The fractions are assayed by UV after diluting them 1:10 with water. On the basis of the UV data, the first two eluates are pooled. The third eluate is saved. The data are presented in Table II below.

Table II

| Sample | Volume | Pseudomonas mildenbergii (UC 3029) | Bacillus subtilis | A | λ |
|---|---|---|---|---|---|
| Spent | 33.4 l | NZ | NZ | 1.4 | 265 nm |
| Wash | 3.5 l | NZ | NZ | 0.24 | 265 |
| 1st Eluate | 320 ml | 21 mm | 20 mm | 0.62 | 265 |
| 2nd Eluate | 2000 ml | 31 | 30 | 5.80 | 260 |
| 3rd Eluate | 2000 ml | 23 | 20 | 2.18 | 255 |
| 4th Eluate | 1000 ml | 18 | NZ | 1.29 | 255 |
| 5th Eluate | 1000 ml | NZ | NZ | 1.13 | 255 |

(3) Desalting

Eluate No. 3 above (2000 ml) is passed over 200 ml granular charcoal in a chromatography tube. The column is washed with 500 ml deoinized water. Neither the spent nor the wash has any UV absorbance. The activities are eluted with 700 ml 25% acetone in water. The eluate is concentrated to an aqueous amounting to 500 ml. A 1:10 dilution of this absorbs strongly at 255 nm. Bioautography on cellulose with methanol shows that gougerotin and antibiotic 354 are present.

(4) Ultrafiltration

The desalted aqueous from above is passed over an Amicon UM 2 ultrafilter (Amicon Corp., 21 Hartwell Avenue, Lexington, MA 02173). The retentate shows no activity and is discarded after a wash of one volume. The first filtrate and wash are pooled and lyophilized. The residue weighs 4.5 gm. This shows a UV max at 252 nm with an inflection at 212 nm on a strong end absorption.

(5) Separation Of Gougerotin From Antibiotic 354

A 68 gm preparation treated essentially as described above (except for the ultrafiltration), assays at 0.68 BU/mg vs. *B. subtilis*; it is labeled Prep. 216-4. Bioautography shows that it contains gougerotin and antibiotic 354.

A cellulose 300 column measuring 5.0 × 150 cm is flushed with methanol at 20 ml/minute (10 psi). The bed volume is 2.9 l.

Thirty grams of the above Prep. 216-4 is dissolved in 65 ml water and the solution is injected onto the column. Some of the solid precipitates when it contacts the methanol but this does not plug the column or otherwise interfere with the procedure. The column is eluted with methanol at 20 ml/minute. The eluate fractions are assayed by UV using 1:10 dilutions. The data are presented in Table III. Fractions 3-8 are pooled and concentrated to give 10.2 gm tan solid. Bioautography shows this to contain antibiotic 354 and no gougerotin. A second injection using the rest of the sample and similarly analyzed yields 12.0 gm of a like preparation.

Table III

| Fraction | Volume | Color | $A_{255-265}$ | *Pseudomonas mildengergii* (UC 3029) |
|---|---|---|---|---|
| 1 | 1300 ml | Colorless | 0.00 | — |
| 2 | 1200 ml | Colorless | 0.21 | — |
| 3 | 400 ml | Colorless | 2.13 | 30 mm |
| 4 | 400 ml | Light Yellow | 9.30 | 40 |
| 5 | 425 ml | Light Yellow | 12.8 | 39 |
| 6 | 500 ml | Light Yellow | 12.4 | 36 |
| 7 | 500 ml | Trace Yellow | 8.4 | 27 |
| 8 | 500 ml | Colorless | 1.12 | 23 |
| 9 | 500 ml | Colorless | — | 20 |
| 10 | 500 ml | Colorless | — | 19 |
| 11 | 500 ml | Colorless | — | trace |

After fraction No. 11 the solvent is switched to water and the elution is continued at 20 ml/minute. The data are presented in Table IV below. Fractions 2 and 3 are pooled and lyophilized to give 17.9 gm tan solid. A second injection yields 22.1 gm. Bioautography shows this to contain only gougerotin.

Table IV

| Fraction | Volume | Color | $A_{269}$ |
|---|---|---|---|
| 1 | 1000 ml | Colorless | 0.30 |
| 2 | 1000 ml | Yellow | 11.0 |
| 3 | 900 ml | Light Yellow | 2.64 |
| 4 | 1400 ml | Colorless | 0.08 |

The 68 gm sample (216-4) gives 22.2 gm (32.6%) antibiotic 354-containing solids and 40 gm (58.8%) gougerotin-containing solids.

The 22 gm of antibiotic 354 material assays at 0.35 BU/mg vs. *B. subtilis* and 0.83 BU/mg vs. UC 3029.

The 22 gm of gougerotin material obtained from the second run assays at 0.5 BU/mg vs. *B. subtilis* and 1.5 BU/mg vs. UC 3029.

Both preparations are grossly impure.

(6) Pure Gougerotin

A pool from two cellulose runs similar to that described above (but ultrafiltered) amounts to 5.8 gm. This is dissolved in 15 ml water and injected onto a 200-400 mesh Amberlite CG-120 ($NH_4^+$) column (Rohm & Haas, Philadelphia, Pennsylvania) measuring 2.5 × 100 cm. This is eluted with a water to 1 M $(NH_4)_2SO_4$ gradient at 12 ml/minute.

Fractions amounting to 25 ml are collected. Every fifth fraction is assayed (100 λ/12.7 mm pad) vs. UC 3029. There is no activity through tube No. 250. The UV assay is done with 1:10 dilutions of every tenth tube. This shows no 265 nm band through tube No. 250. The UV data for subsequent tubes is presented in Table V. The *B. subtilis* zones obtained for tubes 260-370 are very small. Tubes 280-340 are pooled to give 1.4 l solution. This is desalted over 200 ml charcoal in a chromatography tube. The charcoal is washed with water and eluted with 25% acetone in water. The fractions are monitored by UV absorbance at 268 nm. The aqueous eluate is lyophilized to give 1.0 gm of essentially pure gougerotin as a white solid.

Table V

| Fraction | $A_{268}$ | Fraction | $A_{268}$ |
|---|---|---|---|
| 260 | 0.26 | 320 | 1.87 |
| 270 | 0.27 | 330 | — |
| 280 | 0.45 | 340 | 0.68 |
| 290 | 1.30 | 350 | 0.32 |
| 300 | 2.46 | 360 | 0.20 |
| 310 | 2.55 | 370 | 0.15 |

(7) Pure Antibiotic 354 As The Sulfate

A pool is made of various fractions which had been treated as described above through the cellulose column step. It amounts to 3.78 gm and is dissolved in 10 ml water. This is injected onto the CG-120 ($NH_4^+$) column described above for gougerotin and eluted with the same gradient at the same rate. An aliquot of every tenth tube is diluted 1:10 with water and examined by UV and bioassayed. Nothing elutes up to tube No. 220. The data for subsequent tubes are presented in Table VI. Fractions 248-340 are pooled to give 2.5 l solution with $A_{252}$ = 1.27. This is desalted as described for gougerotin using a bed of charcoal measuring 3.5 × 28 cm (270 ml) and monitoring at the appropriate wavelengths. The desalted eluate is lyophilized to give 2.36 gm essentially pure antibiotic 354 as a tan solid. It assays at 8 BU/mg vs. UC 3029.

Table VI

| Fraction | $A_{255}$ | $A_{212}$ | Pseudomonas mildenbergii (UC 3029) |
|---|---|---|---|
| 230 | 0.23 | 1.08 | — |
| 240 | 1.10 | 5.39 | — |
| 250 | 1.60 | 8.20 | — |
| 260 | 1.87 | 8.60 | 35 mm |
| 270 | 2.75 | 10.1 | 40 |
| 280 | 2.05 | 9.00 | 39 |
| 290 | 1.49 | 6.95 | 37 |
| 300 | 1.03 | 4.60 | 33 |
| 310 | 0.69 | 2.41 | 26 |
| 320 | 0.46 | 1.88 | NZ |
| 330 | 0.31 | 1.25 | NZ |
| 340 | 0.20 | 0.82 | NZ |
| 350 | 0.15 | 0.51 | NZ |

EXAMPLE 2 — Acetylation Of Antibiotic 354

A sample of antibiotic 354 is stirred in tetrahydrofuran with pyridine and acetic anhydride. The solvent is removed in vacuo and the residue is partitioned between ethyl acetate and 0.01 N HCl. The aqueous is lyophilized. When the solids are redissolved in water, crystals form and are collected. These crystals are shown by mass spectroscopy to be the mono-N-acetyl-dehydrochlorinated derivative of antibiotic 354.

EXAMPLE 3 — Preparation Of Antibiotic 354.HCl From Antibiotic 354.H$_2$SO$_4$ A 14 mg sample of antibiotic 354.H$_2$SO$_4$ is dissolved in 0.3 ml water and passed over a 0.4 × 8 cm column of 100–200 mesh Dowex 2 × 8 (Cl$^-$). Eluted with distilled water and assayed each 3.0 ml fraction with ninhydrin spray after spotting onto a cellulose tlc (thin layer chromatography) plate and by UV absorption (bands at 251 and 211 in a 1:4 ratio). The appropriate pool is lyophilized. The solid residue is judged to be the hydrochloride by mass spectroscopy.

EXAMPLE 4 — Preparation Of Antibiotic 354.HOAc From A Mix Of Gougerotin And Antibiotic 354

An aqueous carbon eluate (4 l) containing gougerotin and antibiotic 354 is passed over a column of 200 g Dowex 50 W × 8 (H$^+$). The column is washed with deionized water and eluted with 2.0 M pyridinium acetate buffer at pH 5. Fractions 13–17 (45 ml each) are pooled on the basis of bioactivity (12.7 mm pads, agar tray), vs. UC 3029 and lyophilized. The solids give bioautographic patterns indicating that the main activity is antibiotic 354 which must be in the acetate form. The mixture of acetates so obtained is separated into gougerotin acetate and antibiotic 354 acetate by cellulose chromatography as described above.

EXAMPLE 5 — Capsules

One thousand two-piece hard gelatin capsules for oral use, each containing 250 mg of antibiotic 354, are prepared from the following types and amounts of materials:

| | |
|---|---|
| Antibiotic 354 | 250 gm |
| Corn starch | 150 gm |
| Talc | 75 gm |
| Magnesium stearate | 25 gm |

The materials are thoroughly mixed and then encapsulated in the usual manner.

The foregoing capsules are useful for the systemic treatment of infection in adult humans by the oral administration of one capsule every 4 hours.

Using the procedure above, capsules are similarly prepared containing the antibiotic in 50, 100, and 500 mg amounts by substituting 50, 100 and 500 g of antibiotic for the 250 g used above.

EXAMPLE 6 — Tablets

One thousand tablets for oral use, each containing 500 mg of antibiotic 354, are prepared from the following types and amounts of materials:

| | |
|---|---|
| Antibiotic 354 | 500 gm |
| Lactose | 125 gm |
| Corn starch | 65 gm |
| Magnesium stearate | 25 gm |
| Light liquid petrolatum | 3 gm |

The ingredients are thoroughly mixed and slugged. The slugs are broken down by forcing through a number 16 screen. The resulting granules are then compressed into tablets, each tablet containing 500 mg of antibiotic.

The foregoing tablets are useful for systemic treatment of infections in adult humans by oral administration of 1 tablet every 4 hours.

Using the above procedure, except for reducing the amount of antibiotic to 200 g, tablets containing 200 mg of antibiotic are prepared.

EXAMPLE 7 — Tablets

One thousand oral tablets, each containing 125 mg of antibiotic 354 and a total of 250 mg (83.3 mg each) of sulfadiazine, sulfamerazine, and sulfamethazine, are prepared from the following types and amounts of materials:

| | | |
|---|---|---|
| Antibiotic 354 | 125 | gm |
| Sulfadiazine 83.3 | gm | |
| Sulfamerazine | 83.3 | gm |
| Sulfamethazine | 83.3 | gm |
| Lactose | 50 | gm |
| Corn starch | 50 | gm |
| Calcium stearate | 25 | gm |
| Light liquid petrolatum | 5 | gm |

The ingredients are thoroughly mixed and slugged. The slugs are broken down by forcing through a number 16 screen. The resulting granules are then compressed into tablets, each containing 125 mg of antibiotic and a total of 250 mg (83.3 mg each) of sulfadiazine, sulfamerazine, and sulfamethazine.

The foregoing tablets are useful for systemic treatment of infections by the oral administration of four tablets first and then 1 every 6 hours.

For the treatment of urinary infections, the triple sulfas in the above formulation is advantageously replaced by 250 g of sulfamethylthiadiazole or 250 g of sulfacetamide.

EXAMPLE 8 — Granules 2,367 g of a granulation suitable for reconstitution with water prior to use is prepared from the following types and amounts of ingredients:

| | |
|---|---|
| Antibiotic 354 | 150 gm |
| Sucrose, powdered | 2155 gm |
| Flavor | 60 gm |

-continued

| | |
|---|---|
| Sodium metabisulfite | 2 gm |

The antibiotic 354, sugar, flavor, and sodium metabisulfite are mixed together until thoroughly blended. The powder mixture is wetted with water and forced through a screen to form granules. The granules are dried and 23.67 g filled into 60 cc bottles. Prior to use sufficient water is added to the granules to make 60 cc of composition.

The foregoing composition is useful for systemic treatment of infection, particularly in children at a dose of 1 teaspoonful (5 cc) four times daily.

EXAMPLE 9 — Oral Syrup 1,000 cc of an aqueous preparation for oral use, containing in each 5 cc dose, 250 mg of antibiotic 354 is prepared from the following types and amounts of ingredients:

| | |
|---|---|
| Antibiotic 354 | 50 gm |
| Citric acid | 2 gm |
| Benzoic acid | 1 gm |
| Sucrose | 700 gm |
| Tragacanth | 5 gm |
| Lemon oil | 2 gm |
| Deionized water q.s. | 1000 cc |

The citric acid, benzoic acid, sucrose, tragacanth, and lemon oil are dispersed in sufficient water to make 850 cc of solution. The antibiotic is stirred into the syrup until uniformly distributed. Sufficient water is added to make 1,000 cc.

The composition so prepared is useful in the systemic treatment of infection due to *Klebsiella pneumoniae* in adult humans at a dose of 1 or 2 teaspoonfuls 4 times a day.

EXAMPLE 10 — Parenteral Suspension

A sterile aqueous suspension for intramuscular use, containing in 1 cc 200 mg of antibiotic is prepared from the following types and amounts of materials:

| | | |
|---|---|---|
| Antibiotic 354 | 200 | gm |
| Lidocaine hydrochloride | 4 | gm |
| Methylparaben | 2.5 | gm |
| Propylparaben | 0.17 | gm |
| Water for injection q.s. | 1000 | gm |

All of the ingredients, except the antibiotic, are dissolved in the water and the solution sterilized by filtration. To the sterile solution is added the sterilized antibiotic and the final suspension is filled into sterile vials and the vials sealed.

EXAMPLE 11 — Parenteral Solution

A sterile aqueous solution for intramuscular use, containing in 1 cc 150 mg of antibiotic 354, is prepared from the following types and amounts of ingredients:

| | | |
|---|---|---|
| Antibiotic 354 | 150 | gm |
| Lactose | 50 | gm |
| Water for injection q.s. | 1000 | cc |

The antibiotic and lactose are dissolved in the water and the solution sterilized by filtration. The sterile solution, in the amount of 2 cc, is aseptically filled into sterile vials and frozen. The water is removed under high vacuum and the vials containing the lyophilized powder are sealed. Just prior to use, sufficient water for injection to make 2 cc of solution is added to the vial.

EXAMPLE 12 — Topical Ointment 1,000 g of 2 percent ointment is prepared from the following types and amounts of ingredients:

| | |
|---|---|
| Antibiotic 354 | 20 gm |
| Zinc oxide | 50 gm |
| Calamine | 50 gm |
| Liquid petrolatum (heavy) | 250 gm |
| Wool fat | 200 gm |
| White petrolatum q.s. | 1000 gm |

The white petrolatum and wool fat are melted and 100 g of liquid petrolatum added thereto. The antibiotic, zinc oxide and calamine are added to the remaining liquid petrolatum and the mixture milled until the powders are finely divided and uniformly dispersed. The powder mixture is stirred into the white petroleum mixture and stirring continued until the ointment congeals.

The foregoing ointment is usefully applied topically to the skin of mammals for the treatment of infection.

The foregoing composition can be prepared by omitting the zinc oxide and calamine.

Following the procedure above, ointments are similarly prepared containing antibiotic 354 in 0.5, 1.0, and 5 percent amounts by substituting 5, 10, and 50 g of antibiotic for the 20 g used above.

EXAMPLE 13 Troches 10,000 Troches are prepared from the following types and amounts of ingredients:

| | |
|---|---|
| Antibiotic 354 | 100 gm |
| Neomycin sulfate | 50 gm |
| Polymyxin B sulfate (10,000 units/mg) | 1 gm |
| Ethyl aminobenzoate | 50 gm |
| Calcium stearate | 150 gm |
| Powdered sucrose q.s. | 5000 gm |

The powdered materials are mixed thoroughly and then compressed into half gram troches following the usual techniques for the preparation of compressed tablets.

The troches are held in the mouth and allowed to dissolve slowly to provide treatment for the mouth and throat of humans.

EXAMPLE 14 — Mastitis Ointment 1,000 g of an ointment for the treatment of mastitis in dairy cattle is prepared from the following types and amounts of ingredients:

| | | |
|---|---|---|
| Antibiotic 354 | 50 | gm |
| Prednisolone acetate | 0.5 | gm |
| Light liquid petrolatum | 300 | gm |
| Chlorobutanol, anhydrous | 5 | gm |
| Polysorbate 80 | 5 | gm |
| 2% Aluminum monostearate-peanut oil gel | 400 | gm |
| White petrolatum q.s. | 1000 | gm |

The antibiotic and prednisolone acetate are milled with the light liquid petrolatum until finely divided and uniformly dispersed. The chlorobutanol, polysorbate 80, peanut oil gel and white petrolatum are heated to 120° F. to form a melt and the liquid petrolatum dispersion stirred in. With continued stirring the dispersion is allowed to cool (and congeal) to room temperature and is filled into disposable mastitis syringes in 10 g doses.

EXAMPLE 15 — Animal Feed 1,000 g of a feed mix is prepared from the following types and amounts of ingredients:

| Antibiotic 354 | 10 gm |
| --- | --- |
| Soybean meal | 400 gm |
| Fish meal | 400 gm |
| Wheat germ oil | 50 gm |
| Sorghum molasses | 140 gm |

The ingredients are mixed together and pressed into pellets.

The composition can be fed to laboratory animals, i.e., rats, mice, guinea pigs, and rabbits for prophylaxis during shipping.

For larger animals the composition can be added to the animal's regular feed in an amount calculated to give the desired dose of antibiotic.

We claim:

1. An antibacterial composition comprising, in unit dosage form, from about 25 to about 500 mg of antibiotic 354 which in its essentially pure form is characterized as the sulfate salt having the following characteristics:
   (a) molecular weight of 172 (field desorption mass. spec.);
   (b) has the following elemental analysis: C, 37.08; H, 4.79; N, 12.38; Cl, 15.52; S, 7.48; O, 22.75;
   (c) is soluble in water and poorly soluble in methanol, acetone, dimethylsulfoxide and dimethylformamide;
   (d) has a characteristic infrared absorption spectrum when dissolved in a mineral oil mull as shown in FIG. 1 of the drawings;
   (e) has a characteristic ultraviolet absorption spectrum as shown in FIG. 2 of the drawings; and,
   (f) has a characteristic NMR spectrum as shown in FIG. 3 of the drawings, or its pharmacologically acceptable salts as an essentially active ingredient in combination with a pharmaceutical carrier.

2. An antibacterial composition, according to claim 1 comprising from about 5% to about 65% of antibiotic 354.

3. A sterile antibacterial composition for parenteral administration comprising from about 5% to about 65% of antibiotic 354 which in its essentially pure form is characterized as the sulfate salt having the following characteristics:
   (a) molecular weight of 172 (field desorption mass. spec.);
   (b) has the following elemental analysis: C, 37.08; H, 4.79; N, 12.38; Cl, 15.52; S, 7.48; O, 22.75;
   (c) is soluble in water and poorly soluble in methanol, acetone, dimethylsulfoxide and dimethylformamide;
   (d) has a characteristic infrared absorption spectrum when dissolved in a mineral oil mull as shown in FIG. 1 of the drawings;
   (e) has a characteristic ultraviolet absorption spectrum as shown in FIG. 2 of the drawings; and,
   (f) has a characteristic NMR spectrum as shown in FIG. 3 of the drawings,
   or its pharmacologically acceptable salts as an essentially active ingredient in an effective antibacterial amount in combination with a pharmaceutical carrier.

4. The process for treating susceptible microbial antibacterial infectious disease in humans and animals which comprises the administering to the infected host a therapeutic effective antibacterial amount of antibiotic 354 which in its essentially pure form is characterized as the sulfate salt having the following characteristics:
   (a) molecular weight of 172 (field desorption mass. spec.);
   (b) has the following elemental analysis: C, 37.08; H, 4.79; N, 12.38; Cl, 15.52; S, 7.48; O, 22.75;
   (c) is soluble in water and poorly soluble in methanol, acetone, dimethylsulfoxide and dimethylformamide;
   (d) has a characteristic infrared absorption spectrum when dissolved in a mineral oil mull as shown in FIG. 1 of the drawings;
   (e) has a characteristic ultraviolet absorption spectrum as shown in FIG. 2 of the drawings; and,
   (f) has a characteristic NMR spectrum as shown in FIG. 3 of the drawings,
   or its pharmacologically acceptable salts in combination with a pharmaceutical carrier.

5. A process, according to claim 4, wherein antibiotic 354 is administered in unit dosage form in an amount of from about 25 to about 500 mg of said antibiotic in association with a pharmaceutical carrier.

6. A process, according to claim 4, wherein antibiotic 354 is administered to the infected host in unit dosage form in an amount of from about 1 mg/kg/day to about 60 mg/kg/day of said antibiotic in association with a pharmaceutical carrier.

7. A process of prophylactic treatment for the prevention of susceptible antibacterial infectious disease comprising the administering to a disease-susceptible human or animal host an effective antibacterial amount of antibiotic 354 which in its essentially pure form is characterized as the sulfate salt having the following characteristics:
   (a) molecular weight of 172 (field desorption mass. spec.);
   (b) has the following elemental analysis: C, 37.08; H, 4.79; N, 12.38; Cl, 15.52; S, 7.48; O, 22.75;
   (c) is soluble in water and poorly soluble in methanol, acetone, dimethylsulfoxide and dimethylformamide;
   (d) has a characteristic infrared absorption spectrum when dissolved in a mineral oil mull as shown in FIG. 1 of the drawings;
   (e) has a characteristic ultraviolet absorption spectrum as shown in FIG. 2 of the drawings; and,
   (f) has a characteristic NMR spectrum as shown in FIG. 3 of the drawings,
   or its pharmacologically acceptable salts in combination with a pharmaceutical carrier.

8. A process, according to claim 7, wherein antibiotic 354 is administered in unit dosage form in an amount of from about 25 to about 500 mg of said antibiotic in association with a pharmaceutical carrier.

* * * * *